(12) United States Patent
Anraku et al.

(10) Patent No.: US 8,623,655 B2
(45) Date of Patent: Jan. 7, 2014

(54) COMPOSITION FOR PLASMA AND SERUM SEPARATION, AND CONTAINER FOR BLOOD TESTING

(75) Inventors: Hideo Anraku, Shunan (JP); Masatoshi Niunoya, Shunan (JP)

(73) Assignee: Sekisui Medical Co., Ltd., Tokyo (JP)

( * ) Notice: Subject to any disclaimer, the term of this patent is extended or adjusted under 35 U.S.C. 154(b) by 225 days.

(21) Appl. No.: 13/320,782

(22) PCT Filed: Jan. 25, 2011

(86) PCT No.: PCT/JP2011/051300
§ 371 (c)(1),
(2), (4) Date: Nov. 16, 2011

(87) PCT Pub. No.: WO2011/105151
PCT Pub. Date: Sep. 1, 2011

(65) Prior Publication Data
US 2012/0070350 A1    Mar. 22, 2012

(30) Foreign Application Priority Data

Feb. 26, 2010    (JP) ................................. 2010-043140

(51) Int. Cl.
*B01D 43/00*    (2006.01)

(52) U.S. Cl.
USPC ............. 436/16; 436/174; 210/516; 210/782; 137/544

(58) Field of Classification Search
USPC ............. 436/16, 174; 210/516, 782; 137/544
See application file for complete search history.

(56) References Cited

U.S. PATENT DOCUMENTS

| | | | |
|---|---|---|---|
| 4,043,928 A | 8/1977 | Lukacs et al. | |
| 4,083,784 A | 4/1978 | Zine, Jr. | |
| 4,235,725 A * | 11/1980 | Semersky | 210/516 |
| 4,350,593 A | 9/1982 | Kessler | |
| 4,994,393 A * | 2/1991 | Pradhan et al. | 436/8 |
| 8,475,742 B2 * | 7/2013 | Suto et al. | 422/527 |
| 2004/0129631 A1 | 7/2004 | Anraku et al. | |
| 2007/0190148 A1 | 8/2007 | Cronin et al. | |

FOREIGN PATENT DOCUMENTS

| | | |
|---|---|---|
| JP | 10-10122 A | 1/1998 |
| JP | 2002-365281 A | 12/2002 |
| JP | 2003-294731 A | 10/2003 |
| WO | WO-2007/029525 A1 | 3/2007 |
| WO | WO-2011/105253 A1 | 9/2011 |

OTHER PUBLICATIONS

International Search Report for the Application No. PCT/JP2011/051300 mailed Mar. 8, 2011.
International Preliminary Report on Patentability for Application No. PCT/JP2011/051300 mailed Sep. 27, 2012.
Supplementary European Search Report or the Application No. EP 11 74 7115 dated Nov. 7, 2012.
"UCON Base Stocks", DOW, Oct. 2005, pp. 1-2.

* cited by examiner

*Primary Examiner* — Monique Cole
(74) *Attorney, Agent, or Firm* — Cheng Law Group, PLLC

(57) ABSTRACT

The invention provides a serum or plasma separating composition which can compensate for the lack of initial thixotropy even at a reduced inorganic powder concentration and in which crevices or the like are less likely to be created in a partition wall formed of the separating composition after being centrifuged. The serum or plasma separating composition contains a liquid resin component having a partition wall-forming capability, a hydrophilic inorganic powder, a hydrophobic inorganic powder, and an organic compound serving as a thixotropy enhancer, wherein the organic compound is a polyalkylene glycol and/or a derivative thereof and is made of at least one type of polymer.

16 Claims, No Drawings

COMPOSITION FOR PLASMA AND SERUM SEPARATION, AND CONTAINER FOR BLOOD TESTING

TECHNICAL FIELD

This invention relates to compositions and blood testing containers for use in separating serum or plasma from blood, and more particularly relates to a serum or plasma separating composition and a blood testing container both for separating serum or plasma from blood using a difference in specific gravity between blood components.

BACKGROUND ART

Such a technique for separating serum or plasma from blood by centrifugation using a difference in specific gravity between blood components is widely used. To accelerate the separation, various serum or plasma separating compositions have heretofore been proposed.

Compositions presently used as the serum or plasma separating compositions are those having thixotropy. Such a serum or plasma separating composition contained in a testing container can be prevented from moving during transportation or storage because it has thixotropy. Furthermore, after blood is collected in the container, a partition wall made of the serum or plasma separating composition can be formed by centrifugation. The partition wall is less likely to collapse during withdrawal of serum or plasma lying on the partition wall from the container into another container or during transportation or storage of the container.

Patent Literature 1 below discloses separating compositions in which inorganic fine powder is dispersed in a liquid resin component for the purpose of controlling the specific gravity and imparting thixotropy. Examples of the inorganic powder being used in this technique are silicon dioxide-based inorganic powders, such as silica or bentonite, and titanium dioxide-based inorganic powders. The Background Art section of Patent Literature 1 discloses, as examples of the liquid resin component, liquid resins having themselves a liquid form, such as silicone oil, α-olefin-maleic acid diester copolymers, acrylic resins and polyester copolymers.

The separating composition cannot obtain a sufficient value of initial yield stress unless the inorganic powder concentration is high. However, if inorganic powder is contained at a high concentration, the network of hydrogen bonding between inorganic powder particles is strengthened with time, whereby the value of yield stress is increased so much that the separating composition will not exhibit fluidity even when a normal centrifugal force is applied thereto. In addition, if the network density is further increased with time, the separating composition may cause a phase separation into island domains in which the inorganic powder exists at relatively high concentrations and a sea domain lean in inorganic powder. Once a phase separation occurs, the value of yield stress in the island domains are further increased and the components in the island domains become less likely to be fused again with other components in the separating composition. Therefore, during fluidization by centrifugation, the island domains may be fragmented to drift as oily droplets in the blood or the sea domain may be broken up to float as oily films on the blood. Once such oily droplets or oily films are produced, they may contaminate a measurement device to induce measurement errors.

To solve the above problems, in Patent Literatures 1 and 2 below, an organic compound, such as various surfactants including a polyoxyethylene-polyoxypropylene block copolymer and silicone-based surfactants, is contained as a thixotropy enhancer in the separating composition. Thus, the inorganic powder concentration can be reduced and the thixotropy can be stabilized over a long period of time.

However, most of the above organic thixotropy enhancers exhibit water solubility, which presents the problem of elution of the thixotropy enhancer into the blood. As a result, blood cell membranes may be damaged and cellular blood components may thereby leak out to have an adverse effect on test values. Furthermore, the absorption of water in the blood into the separating composition may be promoted to make the separating composition cloudy.

CITATION LIST

Patent Literature

Patent Literature 1: JP-A-H10-10122
Patent Literature 2: U.S. Pat. No. 4,083,784

SUMMARY OF INVENTION

Technical Problem

To obtain a sufficient thixotropy without any organic thixotropy enhancer as described above and by reducing the inorganic fine powder concentration, a possible method is to use much hydrophilic inorganic fine powder which has a higher surface hydroxyl group concentration than hydrophobic inorganic fine powder having a low surface hydroxyl group concentration and has a strong thixotropy-imparting effect.

However, it has been found that if the ratio of hydrophilic inorganic fine powder is high, plasma or hemocyte remains sandwiched in a thin film form in a partition wall made of a separating composition and formed between plasma and hemocyte components by centrifugation, and the partition wall presents such an appearance as if crevices were created therein.

Such a phenomenon is hardly observed if centrifugation is performed after the blood coagulates, i.e., if serum and clot are separated from each other. In contrast, if the blood is centrifuged using an anticoagulant so as not to coagulate the blood, i.e., if plasma and hemocyte components are separated from each other, the above phenomenon extremely often occurs.

It can be assumed that the reason for the above phenomenon is that if the thixotropy of the separating composition is too high in separating plasma and hemocyte from each other, the separating composition fragmented into fragments during centrifugation loses fluidity before being fused together again in a partition wall-forming position and, therefore, presents such an appearance as if crevices were created. In such a case, components leaking through the crevices from the hemocyte lying under the partition wall may move into the plasma lying over the partition wall. In addition, if the ratio of hydrophilic inorganic fine powder is high, water in the blood is likely to be absorbed in the separating composition. Therefore, the separating composition may become cloudy.

An object of the present invention is to provide a serum or plasma separating composition which can compensate for the lack of initial thixotropy even at a reduced inorganic powder concentration and in which crevices or the like are less likely to be created in a partition wall formed by centrifugation, and a blood testing container in which the serum or plasma separating composition is contained.

Solution to Problem

The inventors have dedicated themselves to accomplishing the above task in relation to a serum or plasma separating composition using a liquid resin component having a partition wall-forming capability, a hydrophilic inorganic powder, a hydrophobic inorganic powder, and an organic compound serving as a thixotropy enhancer. As a result, the inventors have found that low molecular weight alkylene glycols, such as propylene glycol commonly known as a thixotropy enhancer, simply enhance the thixotropy-imparting capability of inorganic powder and further increase the crevice-like appearance after centrifugation, but that, surprisingly, if the number average molecular weight of such an alkylene glycol is 500 to 100000, both inclusive, and the alkylene glycol is contained at a concentration of 0.2% to 5% by weight, both inclusive, the partition wall can be kept free from the crevice-like appearance while maintaining the capability to enhance thixotropy, and the inventors thus have completed the present invention.

Specifically, in a first aspect of the present invention, a serum or plasma separating composition is provided which contains: a liquid resin component having a partition wall-forming capability, a hydrophilic inorganic powder, a hydrophobic inorganic powder, and an organic compound serving as a thixotropy enhancer; wherein the organic compound is a polyalkylene glycol and/or a derivative thereof and is made of at least one type of polymer selected from the group consisting of: 1) a homopolymer of a single type of monomer selected from $C_3$ to $C_5$ alkylene oxide monomers, 2) a random copolymer, an altering copolymer, or a periodic copolymer of two or more types of monomers selected from $C_2$ to $C_5$ alkylene oxide monomers, 3) a block copolymer of two or more types of monomers selected from $C_3$ to $C_5$ alkylene oxide monomers, and 4) a graft copolymer of at least one type of polymer selected from the polymers 1) to 3), the polyalkylene glycol and/or the derivative thereof has a number average molecular weight of 500 to 100000, both inclusive, and the content of the polyalkylene glycol and/or the derivative thereof in the total amount of the serum or plasma separating composition is 0.2% to 5% by weight, both inclusive.

In a second aspect of the present invention, a serum or plasma separating composition is provided in which water is further contained into the composition of the first aspect of the invention.

Furthermore, in the serum or plasma separating composition according to the present invention, hydrophilic silica is preferably used as the hydrophilic inorganic powder and hydrophobic silica is preferably used as the hydrophobic inorganic powder.

Moreover, the present invention also provides a blood testing container including: a container body; and the serum or plasma separating composition according to the present invention contained in the container body.

Hereinafter, the present invention will be described in detail.

(Liquid Resin Component)

The liquid resin component in the serum or plasma separating composition of the present invention is not particularly limited, so long as it takes a liquid form at 5° C. or above and has the necessary fluidity and specific gravity to develop the partition wall-forming capability. The fluidity here means that the viscosity measured at 25° C. (at a shear rate of 1 sec$^{-1}$) using a Brookfield rotary viscometer equipped with a cone-and-plate type rotor is 500 Pa·s or less. The specific gravity here refers to the ratio of the density of liquid resin component at 25° C. to the density of water at 25° C. and is from 0.9 to 1.1 and preferably from 1.02 to 1.07. Examples of such a liquid resin component include liquid resins of silicone resins, α-olefin-fumaric acid diester copolymers, acrylic resins, polyesters, copolymers of sebacic acid, 2,2-dimethyl-1,3-propanediol and 1,2-propanediol, polyether polyurethanes, and polyether esters. Alternatively, the liquid resin component used herein may also take the form of a solution obtained by mixing liquids or mixing a solid and a liquid, for example, a liquid mixture of poly-α-pinene polymer and chlorinated hydrocarbon, a liquid mixture of chlorinated polybutene and a liquid compound such as an epoxidized animal or vegetable oil, a liquid mixture of chlorotrifluoroethylene or an alkyl benzenepolycarboxylate ester derivative and polyoxyalkylene glycol or the like, or a liquid mixture of an alkyl benzenepolycarboxylate ester derivative (e.g., a phthalic acid ester, a trimellitic acid ester or a pyromellitic acid ester) and a petroleum resin (also referred to as a petroleum-based hydrocarbon resin) or a DCPD resin (also referred to as a cyclopentadiene-based petroleum resin) made of a un-, partially- or fully-hydrogenated product of a homopolymer or copolymer of $C_5$ fractions (including cyclopentadiene, isoprene, piperylene, and 2-methylbutene-1,2-methylbutene-2) obtained by steam cracking of petroleum oils, a homopolymer or copolymer of $C_9$ fractions (including styrene, vinyl toluene, α-methylstyrene, indene and coumarone) also obtained by steam cracking of petroleum oils, or a copolymer of one or more of the $C_5$ fractions and one or more of the $C_9$ fractions.

(Inorganic Powder)

In the present invention, a hydrophilic inorganic powder and a hydrophobic inorganic powder are used together. These inorganic powders are not particularly limited so long as their particle surfaces are hydrophilic or hydrophobic. Examples of the inorganic powders include silicon dioxide-based fine powders, such as silica produced by known gas-phase processes (also referred to as dry processes) or sedimentation, or clay minerals including bentonite and smectite, titanium dioxide-based fine powders, and alumina-based fine powders.

Titanium dioxide-based inorganic powders, if having an anatase crystal structure, have strong photocatalytic activities and may therefore decompose organic matters, such as the liquid resin component. Therefore, the titanium dioxide-based inorganic powder used herein should preferably have a rutile crystal structure. Furthermore, alumina-based inorganic powders may have an adverse effect on the test value for aluminum contained only in minute amounts in the blood and therefore should be restricted to applications in which aluminum is not measured. Hence, the more preferred inorganic powders are silicon dioxide-based powders, including silica and clay minerals such as bentonite or smectite.

The above inorganic powders generally have hydroxyl groups on their particle surfaces and are therefore hydrophilic. However, hydrophobic inorganic powders will be obtained by treating the surface of the inorganic powders. Whether the particle surface of the inorganic powder is hydrophilic or hydrophobic is generally determined by the state of the inorganic powder upon dispersion into a water-alcohol mixture solvent. If the inorganic powder can be dispersed into pure water, it can be considered hydrophilic. In this case, hydroxyl groups remains on the particle surface as they are.

On the other hand, if the inorganic powder can be dispersed only into water-alcohol mixture solvents, it can be considered hydrophobic.

Examples of alcohols that can be used herein include methanol and ethanol. Hydrophobic inorganic powders that are easy to use are those having a hydrophobicity to such an extent that they can be dispersed into a mixture solvent having an alcohol concentration of 25% by volume or more.

In fact, commonly available hydrophobic inorganic powders are those in which some of hydroxyl groups on the particle surface of a hydrophilic inorganic powder are blocked with alkylsilyl groups, such as dimethylsilyl groups, trimethylsilyl groups or octylsilyl groups, silicone oil or the like.

The ratio of the use of hydrophilic inorganic powder to the use of hydrophobic inorganic powder, i.e., the hydrophilic inorganic powder to hydrophobic inorganic powder ratio, is by weight preferably within the range from 0.2 to 1.0, more preferably within the range from 0.3 to 0.9, and still more preferably within the range from 0.3 to 0.8.

If the hydrophilic and hydrophobic inorganic powders are used within the above ranges, the total concentration of the inorganic powders in the separating composition can be limited to 3% by weight or below. Thus, the separating composition can stably maintain the initial thixotropy over a long period of time.

If the hydrophilic inorganic powder to hydrophobic inorganic powder ratio (by weight) is less than 0.2, the thixotropy-imparting capability of the hydrophilic inorganic powder will be lowered. This requires an increase in the total concentration of the inorganic powders to 3% by weight or more, whereby it becomes difficult for the separating composition to stably maintain the initial thixotropy over a long period of time.

On the other hand, if the hydrophilic inorganic powder to hydrophobic inorganic powder ratio (by weight) is more than 1.0, the total concentration of the inorganic powders can be limited to 3% by weight or below. This may further facilitate that the separating composition stably maintains the initial thixotropy over a long period of time. However, the hydrophilic inorganic powder becomes likely to absorb water in the blood, which may make the separating composition cloudy.

Furthermore, the hydrophilic and hydrophobic inorganic powders are preferably fine powders. The term "fine powder" herein refers to powder whose primary particles have an average particle size (diameter) of 10 µm or less or whose BET specific surface area is 30 m$^2$/g or more. If the inorganic powders are fine powders, they can have a large specific surface area and can thereby effectively impart thixotropy. The BET specific surface area is calculated by a method in which molecules whose adsorption area has been known are adsorbed on the surface of a powder particle at a temperature of liquid nitrogen and the specific surface area of the sample is obtained from the amount of molecules adsorbed on the powder particle surface. Examples of molecules for use in adsorption include nitrogen molecules and argon molecules.

Considering the above various points, it is preferred to use silicon dioxide-based fine powders as the inorganic powders in the present invention. Among the silicon dioxide-based fine powders, the preferred hydrophilic fine powder used is hydrophilic silica powder. Examples of hydrophilic silicas include those produced by gas-phase processes, such as AEROSIL (registered trademark) hydrophilic grades (manufactured by Nippon Aerosil Co., Ltd.) including AEROSIL 130, 200, 300 and OX50, hydrophilic REOLOSIL (registered trademark) (manufactured by Tokuyama Corporation) including REOLOSIL QS-10, QS-20 and QS-30, and WACKER HDK (registered trademark) hydrophilic grades (manufactured by Wacker Asahikasei Silicone Co., Ltd.) including WACKER HDK S13, N20 and T30.

On the other hand, the preferred hydrophobic silicon dioxide-based inorganic powder used is hydrophobic silica powder. Examples of such hydrophobic silicas include those produced by gas-phase processes, such as AEROSIL hydrophobic grades (manufactured by Nippon Aerosil Co., Ltd.) including AEROSIL R972, R974, R805 and R812, hydrophobic REOLOSIL (manufactured by Tokuyama Corporation) including REOLOSIL MT-10, DM-30S, HM-30S, KS-20S and PM-20, and WACKER HDK hydrophobic grades (manufactured by Wacker Asahikasei Silicone Co., Ltd.) including WACKER HDK H15, H18 and H30, and these silicas are easily available and usable.

(Polyalkylene Glycol and/or Derivative Thereof)

The polyalkylene glycol and/or a derivative thereof used in the present invention is at least one type of polymer selected from the group consisting of: 1) a homopolymer of a single type of monomer selected from $C_3$ to $C_5$ alkylene oxide monomers; 2) a random copolymer, an altering copolymer, or a periodic copolymer of two or more types of monomers selected from $C_2$ to $C_5$ alkylene oxide monomers; 3) a block copolymer of two or more types of monomers selected from $C_3$ to $C_5$ alkylene oxide monomers; and 4) a graft copolymer of at least one type of polymer selected from the polymers 1) to 3), and/or a derivative of the polymer.

The above polyalkylene glycols and/or derivatives thereof may be used singularly or in combination of two or more types in the present invention. For example, polyalkylene glycols made of homopolymers and/or their derivatives may be used singularly or in combination of two or more types of them. Likewise, polyalkylene glycols made of random copolymers or block copolymers and/or their derivatives may be used singularly or in combination of two or more types of them. Alternatively, various types of polyalkylene glycols and their derivatives as described above may be used in various combinations.

For periodic copolymers, if their molecule contains a block copolymer region consisting of a $C_2$ ethylene glycol monomer and having a length exceeding 20% of the total molecular chain length, this increases the water solubility and therefore is not preferred.

Furthermore, either of a polyalkylene glycol and/or its derivative having a single hydroxyl group per molecule or a polyalkylene glycol and/or its derivative having more than one hydroxyl groups per molecule can be used depending on the number of hydroxyl groups derived from the number of functional groups of alcohol as a starting material or depending on whether the treatment for blocking the hydroxyl groups with alkyl groups or the like has been performed or not. However, to reduce the water solubility, the number of hydroxyl groups per molecule is preferably three or less.

Examples of polyalkylene glycol derivatives used include those in which their molecule contain a hydrophobic residue, such as alkylene, alkene, alkyne, aromatic ring or dimethyl siloxane, which is introduced for the purpose of blocking the hydroxyl groups or other purposes.

Furthermore, the polyalkylene glycol derivative may contain, instead of or in addition to the hydroxyl groups, hydrogen-bonding polar groups, such as carbonyl groups, amino groups or thiol groups. Also in this case, however, the number of polar groups per molecule is preferably three or less in order to reduce the water solubility.

If the number average molecular weight of the polyalkylene glycol and/or its derivative is smaller than 500, the effect of preventing the occurrence of crevices in a partition wall formed becomes significantly low. Therefore, the number average molecular weight should be at least 500. On the other hand, if the number average molecular weight of the polyalkylene glycol and/or its derivative is too large, the thixotropy-enhancing effect becomes low. Therefore, the number average molecular weight is preferably at most 100000.

In a further preferred embodiment, when a polyalkylene glycol and/or its derivative having two or more hydroxyl groups is used, it more preferably has a number average molecular weight of at least 3000 for the purposes of further reducing the water solubility and avoiding adverse effects on blood test values. For the same reasons, when a polyalkylene glycol and/or its derivatives having a single hydroxyl group is used, it more preferably has a number average molecular weight of at least 1500.

The concentration of the polyalkylene glycol and/or its derivative used should be at most 5% by weight of the total amount of serum or plasma separating composition. If the concentration is above 5% by weight, the thixotropy-enhancing capability can be significantly lost, which makes it difficult to limit the inorganic powder concentration to 3% by weight or below. The concentration is preferably at most 3% by weight, and more preferably at most 2% by weight.

On the other hand, the lower limit of the concentration of the polyalkylene glycol and/or its derivative used is preferably 0.2% by weight, more preferably 0.4% by weight and still more preferably 0.6% by weight in order to prevent the occurrence of crevices in the partition wall with a higher degree of certainty.

Specific examples of polyalkylene glycols having a number average molecular weight of 500 to 100000 and containing no ethylene glycol block include, as polyalkylene glycols having more than one terminal hydroxyl groups, UNIOL (registered trademark) series (manufactured by NOF Corporation), such as UNIOL PB-700, PB-1000, PB-2000, D-700, D-1200, D-4000, TG-1000, TG-3000, TG-4000 and HS-1600D, POLYCERIN (registered trademark) series (manufactured by NOF Corporation), such as POLYCERIN DCB-1000, DCB-2000, DCB-4000, DC-1100, DC-1800E and DC-3000E, UNILUBE (registered trademark) series (manufactured by NOF Corporation), such as UNILUBE DGP-700, and PREMINOL series (manufactured by Asahi Glass Co., Ltd.), such as PREMINOL S3003, S3006, S3011, S4001, S4006, S4011 and S4015.

On the other hand, specific examples of polyalkylene glycol derivatives include UNILUBE series (manufactured by NOF Corporation), such as UNILUBE MB-7, MB-14, MB-38 and MB-700, NEWPOL series (manufactured by Sanyo Chemical Industries, Ltd.), such as NEWPOL LB-285, LB-625, LB-3000 and LB-1800X, and PREMINOL series (manufactured by Asahi Glass Co., Ltd.), such as PREMINOL S1004F and S1005.

Examples of polyalkylene glycol derivatives having an aromatic ring in the molecule include UNIOL DB-530 and UNILUBE 50 DB-22 (both manufactured by NOF Corporation), and examples of polyalkylene glycol derivatives having an allyl group in the molecule include UNISAFE™ PKA-5014 (manufactured by NOF Corporation).

(Water)

In a serum or plasma separating composition provided in accordance with the second aspect of the invention, water is also contained in addition to the liquid resin component having a partition wall-forming capability, the hydrophilic inorganic powder, the hydrophobicity inorganic powder and the polyalkylene glycol and/or its derivative.

Water is coordinated at hydroxyl groups on the surfaces of the inorganic powder particles and acts as a thixotropy enhancer for promoting the formation of a network of hydrogen bonding via hydroxyl groups between adjacent inorganic powder particles. Thus, the total concentration of the inorganic powders can be further reduced.

In respect of use of water, distilled water or deionized water such as ion-exchanged water, only has to be appropriately used and is preferably used at a concentration necessary to coordinate a single water molecule at each hydroxyl group on the surfaces of the inorganic powder particles or higher concentrations.

The following shows some estimates of the above concentration, taking as examples silicon dioxide-based powders suitable for the inorganic powder.

According to Table 2 of Masayoshi Fuji 2003: Functionalization of Particle Surface. Hyomen Kagaku, vol. 24, no. 10, pp. 625-634, the hydroxyl group concentration on the surfaces of hydrophilic silicon dioxide fine powder particles is approximately 3 hydroxyl groups/nm$^2$. According to Kyon Hun Min of Asahi Glass Co., Ltd. et al. 2008: Surface and Internal Hydroxyl Group Density of Porous Silica Gel. The 47th Annual Meeting of The NMR Society of Japan (2008), the surface hydroxyl group density is approximately 6 μmol/m$^2$.

If estimation is now made of the water concentration required for the coordination of hydroxyl groups when hydrophilic silicon dioxide fine powder having a specific surface area of 200 m$^2$/g is contained at a concentration of 1% by weight into the separating composition, the estimated value is approximately 0.02% by weight based on either reference literature just described.

Therefore, it is preferred that water be contained at a concentration of 0.02% by weight or more with respect to approximately 1% by weight of hydrophilic silicon dioxide fine powder having the above specific surface area.

If the water concentration is less than 0.02% by weight, the effect of water as a thixotropy enhancer for promoting the formation of a hydrogen bonding network is diminished. This may make it more difficult to reduce the concentration of silicon dioxide fine powder to be contained.

On the other hand, the maximum water concentration is preferably lower than the saturation concentration of water in the liquid resin component at 25° C. In this manner, even if the separating composition is left stand at low temperatures lower than 0° C., the added water hardly precipitates to make the separating compound cloudy.

(Production Method)

The production method of the serum or plasma separating composition provided in accordance with the first aspect of the invention is not particularly limited. The liquid resin component, the hydrophilic inorganic powder, the hydrophobic inorganic powder and the polyalkylene glycol and/or its derivative need to be mixed together. The mixing process is not particularly limited and any known mixing process, such as a planetary mixer, a roll mil or a homogenizer, can be used.

In the second aspect, water is further contained in the components described in the first aspect. However, at least in adding water, water is preferably added, mixed and dissolved in the liquid resin component at a temperature of 30° C. or above. Furthermore, it is preferred to avoid at least simultaneous addition of water and the hydrophilic inorganic powder. Specifically, if it is attempted to simultaneously add water and the hydrophilic inorganic powder into the liquid resin component, hydrophilic inorganic powder particles may cause strong aggregation via water, which may make it difficult to disperse the hydrophilic inorganic powder into the liquid resin component.

Therefore, it is preferred to first disperse at least the hydrophilic inorganic powder into the liquid component and then add water or to first add water in the liquid component, mix them, dissolve water in the liquid component and then add the remaining components.

(Blood Testing Container)

The shape of the testing container for containing the serum or plasma separating composition of the present invention is not particularly limited. For example, any known tubular container having an opening end and a closed bottom can be used as the testing container.

The material for the container is also not particularly limited. For example, any thermoplastic resin can be used as the material, such as polyethylene, polypropylene, polystyrene, polyacrylate, polymethacrylate or polyethylene terephthalate.

In using the serum or plasma separating composition according to the present invention to separate serum or plasma from blood, the serum or plasma separating composition is previously contained, for example, at the bottom or sidewall of the above blood testing container before blood as a sample is collected into the container.

Then, when the blood sample is centrifuged with a centrifuge, the cellular component in the blood sediments below and serum or plasma is obtained as a supernatant liquid. The serum or plasma separating composition is located in the intermediate layer between the above blood components to form a partition wall separating them from each other.

Note that to separate out the plasma, it is necessary to previously add an anticoagulant, such as alkali metal salts of heparin, ethylenediaminetetraacetic acid or the like, into the blood and/or the blood testing container or previously apply the anticoagulant to the inner wall surface of the container.

On the other hand, to separate out the serum, it is necessary to collect the blood into the blood testing container without using any anticoagulant, coagulate it and then centrifuge it. Note that if the blood coagulation needs to be promoted, it is necessary to previously add fine powder, such as silica or clay minerals including bentonite and smectite, or a material for promoting blood coagulation, such as thrombin, into the blood and/or the blood testing container or previously apply such a material to the inner wall surface of the container.

Advantageous Effects of Invention

The serum or plasma separating composition provided in accordance with the first aspect of the invention is formulated with such a polyalkylene glycol as specified above and/or its derivative at a concentration of 0.2% to 5% by weight, both inclusive, of the total amount of the composition in addition to the liquid resin component, the hydrophilic inorganic powder and the hydrophobic inorganic powder. Therefore, even if the total concentration of the inorganic powders is as low as, for example, not more than about 3% by weight, the separating composition can have a sufficient initial thixotropy to such an extent that it does not move even if the testing container containing the composition is placed sideways for a long time.

Therefore, there hardly occurs an increase in the value of yield stress with time due to an increase in the network density of hydrogen bonding between inorganic powder particles. As a result, the stability of the initial thixotropy over time can be increased, whereby the separating composition reliably exhibits fluidity by a normal centrifugation.

In addition, even if the separating composition is used in separating out plasma using an anticoagulant, crevices are less likely to be created in a partition wall made of the separating medium and formed between the plasma layer and the hemocyte layer. Therefore, the mixing of leaking components from the hemocyte into the plasma is less likely to occur. Furthermore, neither do oily drops drift in the blood, nor do oily films float on the blood surface. Therefore, the analyzer is less likely to be contaminated and to cause measurement errors.

In the serum or plasma separating composition provided in accordance with the second aspect of the invention, such a polyalkylene glycol as specified above and/or its derivative is contained at a concentration of 0.2% to 5% by weight, both inclusive, of the total amount of the composition in addition to the liquid resin component, the hydrophilic inorganic powder, the hydrophobic inorganic powder and water. Therefore, like the serum or plasma separating composition provided in accordance with the first aspect of the invention, even if the total concentration of the inorganic powders is as low as, for example, not more than about 3% by weight, the separating composition will have a sufficient initial thixotropy like the first embodiment. In addition, the initial thixotropy can be stably maintained for a long period of time, the partition wall made of the separating medium is less likely to create crevices, oily drops are less likely to drift in the blood, and oily films are less likely to float on the blood surface.

Note that the term "sufficient initial thixotropy" herein means that the value of yield stress measured at 25° C. (at shear rates of 1 $sec^{-1}$ and 2 $sec^{-1}$) using the above-mentioned rotary viscometer are at least 18 Pa, preferably at least 20 Pa and at most 50 Pa and preferably at most 40 Pa.

Since the testing container according to the present invention contains the serum or plasma separating composition provided in accordance with the first or second aspect, the serum or plasma separating composition is less likely to move during storage and transportation of the blood testing container. This prevents contamination by other chemicals, such as a blood anticoagulant, a blood coagulation promoter or a glycolytic inhibitor, contained in the blood testing container. In addition, since the partition wall made of the separating composition is less likely to collapse after centrifugation, the hemocyte and the serum or plasma once separated away from each other are less likely to be mixed together again. Therefore, individual ingredients in the serum or plasma can be measured with high accuracy.

DESCRIPTION OF EMBODIMENTS

Hereinafter, the present invention will become apparent by reference to specific examples of the invention and comparative examples. Note that the present invention is not limited to the following examples.

The materials used in the examples and comparative examples are as follows.

(Materials Used as Liquid Resin Component)

TABLE 1

<Materials Used as Liquid Components>

| Name | Manufacturer | Trade Name | | Softening Point (° C.) | Viscosity at 25° C. (mPa · s) | Specific Gravity |
|---|---|---|---|---|---|---|
| Cyclopentadiene Oligomer | Exxon Mobil | ESCOREZ | 5690 | 90 | | 1.07 |
| Trimellitic Acid Ester | Dainippon Ink And Chemicals, Incorporated | Monocizer | W700 | | 220 | 0.99 |

(Materials Used as Inorganic Powder)

TABLE 2

<Materials Used as Inorganic Fine Powder>

| Name | Manufacturer | Trade Name | | Specific Surface Area ($m^2/g$) | Density ($g/cm^3$) |
|---|---|---|---|---|---|
| Hydrophilic Fine-Powdered Silica (Gas-Phase Process) | Nippon Aerosil Co., Ltd. | AEROSIL | 200CF | 200 | 2.2 |
| Hydrophobic Fine-Powdered Silica (Gas-Phase Process) | Nippon Aerosil Co., Ltd. | AEROSIL | R974 | 170 | 2.2 |

(Materials Used as Polyalkylene Glycol and/or its Derivative)

TABLE 3

<Materials Used as Polyalkylene Glycol>

| Name | Manufacturer | Trade Name | | Number of Hydroxyl Groups | Molecular Weight | Number Average Molecular Weight |
|---|---|---|---|---|---|---|
| Propylene Glycol | Wako Pure Chemical Industries, Ltd. | Propylene Glycol | | 2 | 76 | |
| Polypropylene Glycol | NOF Corporation | UNIOL | D250 | 2 | | 250 |
| Polypropylene Glycol | NOF Corporation | UNIOL | D400 | 2 | | 400 |
| Polypropylene Glycol | NOF Corporation | UNIOL | D700 | 2 | | 700 |
| Polypropylene Glycol | NOF Corporation | UNIOL | D1000 | 2 | | 1000 |
| Polypropylene Glycol | NOF Corporation | UNIOL | D1200 | 2 | | 1200 |
| Polypropylene Glycol | NOF Corporation | UNIOL | D4000 | 2 | | 4000 |

(Material Used as Blood Anticoagulant Applied to Inner Wall Surface of Testing Container)

TABLE 4

<Material Used as Blood Anticoagulant Applied to Inner Wall Surface of Testing Container>

| Name | Manufacturer | Trade Name |
|---|---|---|
| Lithium Heparin | Wako Pure Chemical Industries. Ltd. | Heparin Lithium |

EXAMPLE 1

Cyclopentadiene oligomer (Trade Name: ESCOREZ5690, manufactured by Exxon Mobil) and trimellitic acid ester (Trade Name: Monocizer W700, manufactured by Dainippon Ink And Chemicals, Incorporated) were dissolved at 130° C., thereby preparing a liquid resin component. Polypropylene glycol (Trade Name: UNIOL D700, manufactured by NOF Corporation) was dissolved as a polyalkylene glycol in the obtained liquid resin component and the solution was cooled to approximately 30° C. Next, hydrophilic fine-powdered silica (Trade Name: AEROSIL 20005, manufactured by Nippon Aerosil Co., Ltd.) and hydrophobic fine-powdered silica (Trade Name: AEROSIL R974, manufactured by Nippon Aerosil Co., Ltd.) were dispersed as inorganic powders into the liquid resin component while stirring the liquid resin component with a planetary mixer. In this manner, a serum or plasma separating composition of Example 1 was obtained. The formulation ratio of components is as shown in Table 5 below.

EXAMPLES 2 TO 4 AND COMPARATIVE EXAMPLES 1 TO 4

Serum or plasma separating compositions were obtained in the same manner as in Example 1, except that the formulation ratio of components varied as shown in Table 5.

TABLE 5

<Formulation Ratio of Components in Examples and Comparative Examples (% by weight)>

| | | Examples | | | | Comparative Examples | | | |
|---|---|---|---|---|---|---|---|---|---|
| | | 1 | 2 | 3 | 4 | 1 | 2 | 3 | 4 |
| ESCOREZ | 5690 | 52.3 | 52.3 | 52.3 | 52.3 | 52.3 | 52.3 | 52.3 | 52.3 |
| AEROSIL | 200CF | 1.0 | 1.0 | 1.0 | 1.0 | 1.3 | 1.0 | 1.0 | 1.0 |
| AEROSIL | R974 | 1.7 | 1.7 | 1.7 | 1.7 | 2.2 | 1.7 | 1.7 | 1.7 |
| Propylene Glycol | | | | | | | 0.8 | | |
| UNIOL | D250 | | | | | | | 0.8 | |
| UNIOL | D400 | | | | | | | | 0.8 |
| UNIOL | D700 | 0.8 | | | | | | | |

TABLE 5-continued

<Formulation Ratio of Components in Examples and Comparative Examples (% by weight)>

|  |  | Examples | | | | Comparative Examples | | | |
| --- | --- | --- | --- | --- | --- | --- | --- | --- | --- |
|  |  | 1 | 2 | 3 | 4 | 1 | 2 | 3 | 4 |
| UNIOL | D1000 |  | 0.8 |  |  |  |  |  |  |
| UNIOL | D1200 |  |  | 0.8 |  |  |  |  |  |
| UNIOL | D4000 |  |  |  | 0.8 |  |  |  |  |
| Total Concentration of Fine-Powdered Silicas (%) |  | 2.7 | 2.7 | 2.7 | 2.7 | 3.5 | 2.7 | 2.7 | 2.7 |
| Hydrophilic Fine-Powdered Silica/Hydrophobic Fine-Powdered Silica |  | 0.6 | 0.6 | 0.6 | 0.6 | 0.6 | 0.6 | 0.6 | 0.6 |

(Production of Blood Testing Container Containing Separating Composition)

Each of the above separating compositions was contained in ten 10 mL polyethylene terephthalate-made test tubes (16 mm diameter by 100 mm length) in an amount of approximately 1.2 g for each tube, thereby preparing ten blood testing containers.

Furthermore, each of the above separating compositions was contained in ten 7 mL polyethylene terephthalate-made test tubes (13 mm diameter by 100 mm length) in amount of approximately 0.9 g for each tube, 3000 IU/mL of aqueous solution of lithium heparin was sprayed to the inner wall surface of each test tube in a rate of approximately 18 mg per tube, and the solution was dried, thereby preparing ten blood testing containers.

(Evaluation Method)

1) The specific gravity of each separating composition at 25° C. was measured by a sink-float method.

2) The set of the ten 10 mL blood testing containers prepared for each separating composition were divided into two groups, and the set of the ten 7 mL blood testing containers prepared for each separating composition were likewise divided into two groups. One of the two groups divided for each set were preserved lying sideways at a room temperature of 25° C. for one week, whereas the other group were preserved lying sideways at a room temperature of 25° C. for six months. These preserved samples were evaluated in terms of viscous properties, fluidity resistance and blood separation properties in the following manners.

2-1) Viscous Properties

An amount of approximately 0.5 g of separating composition was recovered from one blood testing container in each 7 mL blood testing container group so as not to knead it to the greatest extent possible, and the viscosity (at a shear rate of 1 sec$^{-1}$) and value of yield stress (at shear rates of 1 sec$^{-1}$ and 2 sec$^{-1}$) of the composition at 25° C. were measured with a Brookfield rotary viscometer equipped with a cone-and-plate type rotor.

2-2) Fluidity Resistance

All of five blood testing containers in each 10 mL blood testing container group were held at 60° C. for 24 hours with their top ends facing obliquely downward at 45 degrees, the separating compositions were measured in terms of their respective moving distances from the initial liquid levels to the leading ends in 24 hours, and the average of the measured values was calculated. In addition, the presence or absence of seepage of the liquid component from the separating composition was evaluated as the presence or absence of phase separation.

2-3) Blood Separation Properties

An amount of 3 mL of volunteer human fresh blood was collected into each of the remaining four blood testing containers in each 7 mL blood testing container group and mixed with the separating composition by turning the container upside down, and the mixture was then centrifuged at 1700 G for five minutes at 20° C.

Thereafter, visual inspection was made of the separating conditions of plasma and hemocyte components separated by the partition wall made of the separating medium and formed by centrifugation, the presence or absence of hemolysis, and the presence or absence of oily suspended matter and oily film.

Note that the evaluation of the separating conditions was implemented by evaluating the mobility of the separating composition, which will move to the partition wall-forming position, in three score levels shown in Table 6 below and also evaluating the degree of crevice-like appearance created in the partition wall into three score levels shown in Table 7 below.

TABLE 6

<Score Table of Mobilities of Separating Compositions>

| Mobility to Partition Wall-Forming Position | Score |
| --- | --- |
| Almost all of the separating composition has moved to the partition wall-forming position. | 3 |
| Part of the separating composition has been left at the container bottom and inner wall surface under the partition wall. | 2 |
| Almost all of the separating composition has been left at the container bottom and inner wall surface under the partition wall. | 1 |

TABLE 7

<Score Table of Crevice-Like Appearances of Partition Walls>

| Degree of Crevice-Like Appearance | Score |
| --- | --- |
| Partition wall presents a clear crevice-like appearance. | 3 |
| Partition wall slightly presents a crevice-like appearance. | 2 |
| Partition wall presents substantially no crevice-like appearance. | 1 |

(Evaluation Results)

The evaluation results of Examples 1 to 4 and Comparative Examples 1 to 4 were put together in Tables 8 to 10.

TABLE 8

Evaluation of Separating Compositions upon Preparation

|  | Examples | | | | Comparative Examples | | | |
| --- | --- | --- | --- | --- | --- | --- | --- | --- |
|  | 1 | 2 | 3 | 4 | 1 | 2 | 3 | 4 |
| Specific Gravity | 1.05 | 1.05 | 1.05 | 1.05 | 1.05 | 1.05 | 1.05 | 1.05 |

TABLE 9

Evaluation of Testing Containers When Preserved Sideways at about 25° C. for One Week after Preparation

|  |  | Examples | | | | Comparative Examples | | | |
| --- | --- | --- | --- | --- | --- | --- | --- | --- | --- |
|  |  | 1 | 2 | 3 | 4 | 1 | 2 | 3 | 4 |
| Viscous Properties at 25° C. | Viscosity (Pa · s) | 163 | 165 | 164 | 162 | 167 | 164 | 160 | 165 |
|  | Value of Yield Stress (Pa) | 27 | 28 | 29 | 27 | 31 | 29 | 28 | 27 |
| Fluidity Resistance | Moving Distance (mm) | 0 | 1 | 0 | 1 | 0 | 0 | 1 | 1 |
|  | Phase Separation | Absent | Absent | Absent | Absent | Absent | Present | Present | Absent |
| Separating Conditions | Mobility to Partition Wall-Forming Position | 3 | 3 | 3 | 3 | 3 | 3 | 3 | 3 |
|  | Degree of Crevice-Like Appearance | 1 | 1 | 1 | 1 | 3 | 3 | 3 | 2 |
| Hemolysis |  | Absent | Absent | Absent | Absent | Absent | Absent | Absent | Absent |
| Oily Suspended Matter or Oily Film |  | Absent | Absent | Absent | Absent | Absent | Absent | Absent | Absent |

TABLE 10

Evaluation of Testing Containers When Preserved Sideways at about 25° C. for Six Months after Preparation

|  |  | Examples | | | | Comparative Examples | | | |
| --- | --- | --- | --- | --- | --- | --- | --- | --- | --- |
|  |  | 1 | 2 | 3 | 4 | 1 | 2 | 3 | 4 |
| Viscous Properties at 25° C. | Viscosity (Pa · s) | 176 | 174 | 177 | 178 | 185 | 175 | 175 | 177 |
|  | Value of Yield Stress (Pa) | 31 | 33 | 32 | 31 | 47 | 32 | 33 | 34 |
| Fluidity Resistance | Moving Distance (mm) | 1 | 0 | 0 | 1 | 0 | 0 | 0 | 0 |
|  | Phase Separation | Absent | Absent | Absent | Absent | Absent | Present | Present | Absent |
| Separating Conditions | Mobility to Partition Wall-Forming Position | 3 | 3 | 3 | 3 | 2 | 3 | 3 | 3 |
|  | Degree of Crevice-Like Appearance | 1 | 1 | 1 | 1 | 3 | 3 | 3 | 2 |
| Hemolysis |  | Absent | Absent | Absent | Absent | Absent | Absent | Absent | Absent |
| Oily Suspended Matter or Oily Film |  | Absent | Absent | Absent | Absent | Absent | Absent | Absent | Absent |

In Examples 1 to 4 and Comparative Examples 2 to 4, to prevent the increase in yield value due to silica aggregation with time, the total content of hydrophilic and hydrophobic silicas was reduced to 2.7% by weight and the hydrophilic inorganic powder to hydrophobic inorganic powder ratio was set at 0.6. Meanwhile, different polyalkylene glycols of different number average molecular weights were added at a rate of 0.8% by weight in the separating compositions. In contrast, only in Comparative Example 1, no polyalkylene glycol was added, the total content of hydrophilic and hydrophobic silicas was increased to 3.5% by weight to compensate for the lack of thixotropy, and the hydrophilic inorganic powder to hydrophobic inorganic powder ratio was set at 0.6.

All of Examples 1 to 4 and Comparative Examples 1 to 4 exhibited sufficient thixotropy and fluidity resistance. In Comparative Example 1, however, the increase in viscous properties during preservation at 25° C. largely exceeded those in the other examples since the total content of hydrophilic and hydrophobic silicas was over 3% by weight. Furthermore, in Comparative Examples 2 and 3, phase separation was observed.

On the other hand, in the blood evaluation using fresh human bloods, Comparative Examples 2 to 4 containing a polyalkylene glycol of number average molecular weight of below 500 and Comparative Example 1 containing no polyalkylene glycol but having a total content of hydrophilic and hydrophobic silicas of over 3% by weight exhibited crevice-like appearances in their partition walls after being centrifuged. In contrast, in Examples 1 to 4 containing polypropylene glycol of number average molecular weight of 700 or more, no crevice-like appearance was observed.

Furthermore, in Comparative Example 1, the fluidity of the separating composition was deteriorated with time.

It has been found from the above that the serum or plasma separating compositions of Examples 1 to 4 are less likely to cause the increase in yield value with time due to increase in the network density of hydrogen bonding between inorganic fine powder particles and can stably maintain the initial thixotropy over a long period of time. In addition, it has also been found that the problem of the fluidity being not exhibited by a normal centrifugation intensity over time does not arise.

Furthermore, it has been found that also if the separating compositions of Examples 1 to 4 are used as plasma separating compositions for the separation of anticoagulated blood, the separating partition wall formed between the plasma and hemocyte layers presents no crevice-like appearance, which avoids that the components leaking from hemocyte are dispersed through the partition wall and then mixed into the plasma. Moreover, it has also been found that a phenomenon does not occur where the composition components released during centrifugation draft as oil droplets in the blood or float in oil film form on the blood surface owing to reaggregation of inorganic fine power particles, and therefore there is no troublesome problem of the released components adhering to the reaction cell or the surface of the electrolysis measurement electrode of an analyzer and contaminating them to induce measurement errors.

Next, a description is given of Examples 5 to 8 and Comparative Examples 5 to 7.

EXAMPLE 5

Cyclopentadiene oligomer (Trade Name: ESCOREZ5690, manufactured by Exxon Mobil) and trimellitic acid ester (Trade Name: Monocizer W700, manufactured by Dainippon Ink And Chemicals, Incorporated) were dissolved at 130° C., thereby preparing a liquid resin component. Polypropylene glycol (Trade Name: UNIOL D4000, manufactured by NOF Corporation) was dissolved as a polyalkylene glycol in the obtained liquid resin component and the solution was cooled to approximately 30° C. Next, hydrophilic fine-powdered silica (Trade Name: AEROSIL 200CF, manufactured by Nippon Aerosil Co., Ltd.) and hydrophobic fine-powdered silica (Trade Name: AEROSIL R974, manufactured by Nippon Aerosil Co., Ltd.) were dispersed as inorganic powders into the liquid resin component while stirring the liquid resin component with a planetary mixer. In this manner, a serum or plasma separating composition of Example 5 was obtained. The formulation ratio of components is as shown in Table 11 below.

EXAMPLES 6 TO 8 AND COMPARATIVE EXAMPLES 5 TO 7

Serum or plasma separating compositions were obtained in the same manner as in Example 5, except that the formulation ratio of components varied as shown in Table 11.

TABLE 11

| | | (Unit of Formulation Ratio: % by weight) | | | | | | |
|---|---|---|---|---|---|---|---|---|
| | | Examples | | | | Comparative Examples | | |
| | | 5 | 6 | 7 | 8 | 5 | 6 | 7 |
| ESCOREZ | 5690 | 52.3 | 52.3 | 52.3 | 52.3 | 52.3 | 52.3 | 52.3 |
| Monocizer | W700 | 44.7 | 44.0 | 43.0 | 41.0 | 44.1 | 39.0 | 35.0 |
| AEROSIL | 200CF | 1.0 | 1.0 | 1.0 | 1.0 | 1.3 | 1.0 | 1.0 |
| AEROSIL | R974 | 1.7 | 1.7 | 1.7 | 1.7 | 2.2 | 1.7 | 1.7 |
| UNIOL | D4000 | 0.3 | 1.0 | 2.0 | 4.0 | 0.1 | 6.0 | 10.0 |
| Total Concentration of Fine-Powdered Silicas (% by weight) | | 2.7 | 2.7 | 2.7 | 2.7 | 3.5 | 2.7 | 2.7 |
| Hydrophilic Fine-Powdered Silica/ Hydrophobic Fine-Powdered Silica | | 0.6 | 0.6 | 0.6 | 0.6 | 0.6 | 0.6 | 0.6 |

The preparation method of blood testing containers containing separating compositions and the evaluation method were implemented in accordance with Example 1. Note, however, that the evaluation was made of blood testing containers when preserved sideways at about 25° C. for one week after preparation.

(Evaluation Results)

The evaluation results of Examples 5 to 8 and Comparative Examples 5 to 7 were put together in Table 12.

TABLE 12

Evaluation Results of Serum or Plasma Separating Compositions of Examples and Comparative Examples When Preserved Sideways at about 25° C. for One Week

| | | Examples | | | | Comparative Examples | | |
|---|---|---|---|---|---|---|---|---|
| | | 5 | 6 | 7 | 8 | 5 | 6 | 7 |
| Viscous Properties at 25° C. | Viscosity (Pa · s) | 170 | 160 | 155 | 160 | 140 | 160 | 150 |
| | Value of Yield Stress (Pa) | 35 | 30 | 25 | 20 | 18 | 18 | 16 |
| Fluidity Resistance | Moving Distance (mm) | 0 | 0 | 1 | 1 | 3 | 5 | 7 |
| | Phase Separation | Absent | Absent | Absent | Absent | Absent | Present | Present |
| Separating Conditions | Mobility to Partition Wall-Forming Position | 3 | 3 | 3 | 3 | 3 | 3 | 3 |
| | Degree of Crevice-Like Appearance | 1 | 1 | 1 | 1 | 3 | 1 | 1 |
| Hemolysis | | Absent | Absent | Absent | Absent | Absent | Absent | Absent |
| Oily Suspended Matter or Oily Film | | Absent | Absent | Absent | Absent | Absent | Absent | Absent |

In Examples 5 to 8 and Comparative Examples 5 to 7, to prevent the increase in yield value due to silica aggregation with time, the total content of hydrophilic and hydrophobic silicas was reduced to 2.7% by weight and the hydrophilic inorganic powder to hydrophobic inorganic powder ratio was set at 0.6. Meanwhile, polyalkylene glycol of number average molecular weight of 4000 was added at different rates of % by weight in the above separating compositions.

All of Examples 5 to 8 exhibited sufficient thixotropy and fluidity resistance, whereas Comparative Examples 6 and 7 were lack in thixotropy and fluidity resistance. Furthermore, in Comparative Examples 6 and 7, phase separation was observed.

On the other hand, in the blood evaluation using fresh human bloods, Examples 5 to 8 and Comparative Examples 6 and 7, each of which contains 0.3% by weight or more of polyalkylene glycol, exhibited no crevice-like appearance in their partition walls after being centrifuged, but Comparative Example 5 exhibited a crevice-like appearance.

In respect of the mobility to partition wall-forming position, the presence/absence of hemolysis and the presence/absence of oily suspended matter or oil film, all of Examples 5 to 8 and Comparative Examples 5 to 7 were satisfactory.

It has been found from the above that the serum or plasma separating compositions of Examples 5 to 8 maintain sufficient thixotropy and fluidity resistance and simultaneously present no crevice-like appearance in the partition wall after being centrifuged.

Next, a description is given of Examples 9 to 12 and Comparative Examples 8 to 10.

EXAMPLE 9

Cyclopentadiene oligomer (Trade Name: ESCOREZ5690, manufactured by Exxon Mobil) and trimellitic acid ester (Trade Name: Monocizer W700, manufactured by Dainippon Ink And Chemicals, Incorporated) were dissolved at 130° C., thereby preparing a liquid resin component. Polypropylene glycol (Trade Name: UNIOL D4000, manufactured by NOF Corporation) was dissolved as a polyalkylene glycol in the obtained liquid resin component and the solution was cooled to approximately 30° C. Next, hydrophilic fine-powdered silica (Trade Name: AEROSIL 200CF, manufactured by Nippon Aerosil Co., Ltd.) and hydrophobic fine-powdered silica (Trade Name: AEROSIL R974, manufactured by Nippon Aerosil Co., Ltd.) were dispersed as inorganic powders into the liquid resin component while stirring the liquid resin component with a planetary mixer. In this manner, a serum or plasma separating composition of Example 9 was obtained. The formulation ratio of components is as shown in Table 13 below.

EXAMPLES 10 TO 12 AND COMPARATIVE EXAMPLES 8 TO 10

Serum or plasma separating compositions were obtained in the same manner as in Example 9, except that the formulation ratio of components varied as shown in Table 13.

TABLE 13

| | | (Unit of Formulation Ratio: % by weight) | | | | | | |
|---|---|---|---|---|---|---|---|---|
| | | Examples | | | | Comparative Examples | | |
| | | 9 | 10 | 11 | 12 | 8 | 9 | 10 |
| ESCOREZ | 5690 | 52.3 | 52.3 | 52.3 | 52.3 | 52.3 | 52.3 | 52.3 |
| Monocizer | W700 | 44.2 | 44.2 | 44.2 | 44.2 | 44.2 | 44.2 | 44.2 |
| AEROSIL | 200CF | 0.45 | 0.90 | 1.10 | 1.30 | 0.25 | 1.40 | 1.80 |
| AEROSIL | R974 | 2.25 | 1.80 | 1.60 | 1.40 | 2.45 | 1.30 | 0.90 |
| UNIOL | D4000 | 0.8 | 0.8 | 0.8 | 0.8 | 0.8 | 0.8 | 0.8 |
| Total Concentration of Fine-Powdered Silicas (% by weight) | | 2.7 | 2.7 | 2.7 | 2.7 | 2.7 | 2.7 | 2.7 |
| Hydrophilic Fine-Powdered Silica/ Hydrophobic Fine-Powdered Silica | | 0.2 | 0.5 | 0.7 | 0.9 | 0.1 | 1.1 | 2.0 |

The preparation method of blood testing containers containing separating compositions and the evaluation method were implemented in accordance with Example 1. Note, however, that the evaluation was made of blood testing containers when preserved sideways at about 25° C. for one week after preparation.

In respect of the cloudiness of partition wall, the presence or absence of cloudiness of the partition wall was visually inspected after the blood collection tube into which the blood was collected was refrigerated at 4° C. for one month.

(Evaluation Results)

The evaluation results of Examples 9 to 12 and Comparative Examples 8 to 10 were put together in Table 14.

TABLE 14

Evaluation Results of Serum or Plasma Separating Compositions of Examples and Comparative Examples When Preserved Sideways at about 25° C. for One Week

| | | Examples | | | | Comparative Examples | | |
|---|---|---|---|---|---|---|---|---|
| | | 9 | 10 | 11 | 12 | 8 | 9 | 10 |
| Viscous Properties at 25° C. | Viscosity (Pa · s) | 155 | 160 | 170 | 180 | 145 | 190 | 270 |
| | Value of Yield Stress (Pa) | 23 | 28 | 28 | 32 | 16 | 33 | 38 |
| Fluidity Resistance | Moving Distance (mm) | 1 | 1 | 1 | 1 | 20 | 0 | 0 |
| | Phase Separation | Absent | Absent | Absent | Absent | Present | Absent | Absent |
| Separating Conditions | Mobility to Partition Wall-Forming Position | 3 | 3 | 3 | 3 | 3 | 3 | 3 |
| | Degree of Crevice-Like Appearance | 1 | 1 | 1 | 1 | 1 | 1 | 1 |
| | Cloudiness of Partition Wall | Absent | Absent | Absent | Absent | Absent | Present | Present |
| Hemolysis | | Absent | Absent | Absent | Absent | Absent | Absent | Absent |
| Oily Suspended Matter or Oily Film | | Absent | Absent | Absent | Absent | Absent | Absent | Absent |

In Examples 9 to 12 and Comparative Examples 8 to 10, to prevent the increase in value of yield stress due to silica aggregation with time, the total content of hydrophilic and hydrophobic silicas was reduced to 2.7% by weight and the hydrophilic inorganic powder to hydrophobic inorganic powder ratio was set at various values. Furthermore, polyalkylene glycol of number average molecular weight of 4000 was added at a rate of 0.8% by weight in the above separating compositions.

All of Examples 9 to 12 and Comparative Examples 9 and 10 exhibited sufficient thixotropy and fluidity resistance, whereas Comparative Example 8 was lack in thixotropy and fluidity resistance and exhibited phase separation.

On the other hand, in the blood evaluation using fresh human bloods, all of Examples 9 to 12 and Comparative Examples 8 to 10 exhibited no crevice-like appearance in their partition walls after being centrifuged, and were satisfactory in respect of the mobility to partition wall-forming position, the presence/absence of hemolysis and the presence/absence of oily suspended matter or oil film.

In Comparative Examples 9 and 10, however, cloudiness occurred in the partition walls one month after refrigeration at 4° C.

It has been found from the above that the serum or plasma separating compositions of Examples 9 to 12 maintain sufficient thixotropy and fluidity resistance and simultaneously present no cloudiness in the partition walls even after the blood collection tubes after blood collection is preserved at 4° C. for one month.

Next, a description is given of Examples 13 to 19.

The materials used in these examples are as follows.

(Materials Used as Liquid Resin Component)

TABLE 15

| Name | Manufacturer | Trade Name | | Softening Point (° C.) | Viscosity at 25° C. (mPa·s) | Specific Gravity |
|---|---|---|---|---|---|---|
| Cyclopentadiene Oligomer | Exxon Mobil | ESCOREZ | 5690 | 90 | | 1.07 |
| Cyclopentadiene Oligomer | Exxon Mobil | ESCOREZ | 5380 | 85 | | 1.07 |
| Petroleum Resin | KOLON | SUKOREZ | SU90 | 90 | | 1.10 |
| Petroleum Resin | KOLON | SUKOREZ | SU490 | 90 | | 1.09 |
| Petroleum Resin | KOLON | SUKOREZ | SU500 | 100 | | 1.08 |
| Petroleum Resin | KOLON | SUKOREZ | SU100S | 100 | | 1.08 |
| Petroleum Resin | EASTMAN CHEMICAL | REGALITE | S5090 | 90 | | 1.03 |
| Petroleum Resin | EASTMAN CHEMICAL | KLISTALEX | 3085 | 85 | | 1.06 |
| Petroleum Resin | IDEMITSU KOSAN | I-MARV | P-100 | 100 | | 1.03 |
| Trimellitic Acid Ester | J-PLUS | TOTM | TOTM NB | | 180 | 0.99 |

(Material Used as Polyalkylene Glycol and/or its Derivative)

TABLE 16

| Name | Manufacturer | Trade Name | Number of Hydroxyl Groups | Number Average Molecular Weight |
|---|---|---|---|---|
| Polypropylene Glycol | Asahi Glass Co., Ltd. | PREMINOL S3011 | 3 | 10000 |

EXAMPLE 13

Cyclopentadiene oligomers (Trade Name: ESCOREZ5690 and ESCOREZ5380, manufactured by Exxon Mobil) and trimellitic acid ester (Trade Name: TOTM MB, manufactured by J-PLUS Co., Ltd.) were dissolved at 130° C., thereby preparing a liquid resin component. Polypropylene glycol (Trade Name: PREMINOL S3011, manufactured by Asahi Glass Co., Ltd.) was dissolved as a polyalkylene glycol in the obtained liquid resin component and the solution was cooled to approximately 30° C. Next, hydrophilic fine-powdered silica (Trade Name: AEROSIL 200CF, manufactured by Nippon Aerosil Co., Ltd.) and hydrophobic fine-powdered silica (Trade Name: AEROSIL R974, manufactured by Nippon Aerosil Co., Ltd.) were dispersed as inorganic powders into the liquid resin component while stirring the liquid resin component with a planetary mixer. In this manner, a serum or plasma separating composition of Example 13 was obtained. The formulation ratio of components is as shown in Table 17 below.

EXAMPLES 14 TO 19

Serum or plasma separating compositions were obtained in the same manner as in Example 13, except that the formulation ratio of components varied as shown in Table 17.

TABLE 17

| | | (Unit of Formulation Ratio: % by weight) Examples | | | | | | |
|---|---|---|---|---|---|---|---|---|
| | | 13 | 14 | 15 | 16 | 17 | 18 | 19 |
| ESCOREZ | 5690 | 25.0 | 25.0 | | | | | |
| ESCOREZ | 5380 | 26.0 | 26.0 | | | | | |
| SUKOREZ | SU90 | | | 11.0 | 20.0 | 20.0 | 20.0 | 20.0 |
| SUKOREZ | SU490 | | | 25.0 | | | | |
| SUKOREZ | SU500 | | | | 18.0 | | | |
| SUKOREZ | SU100S | | | | | 20.0 | | |
| REGALITE | S5090 | | | 15.0 | 13.0 | 11.0 | 6.0 | |
| KLISTALEX | 3085 | | | | | | 25.0 | 26.0 |
| I-MARV | P-100 | | | | | | | 5.0 |
| TOTM | TOTM NB | 45.5 | 45.4 | 45.4 | 45.4 | 45.4 | 45.4 | 45.4 |
| AEROSIL | 200CF | 1.10 | 1.10 | 0.80 | 0.80 | 0.80 | 1.10 | 1.10 |
| AEROSIL | R974 | 1.60 | 1.60 | 1.90 | 1.90 | 1.90 | 1.60 | 1.60 |
| PREMINOL | S3011 | 0.8 | 0.8 | 0.8 | 0.8 | 0.8 | 0.8 | 0.8 |
| Purified Water | | | 0.1 | 0.1 | 0.1 | 0.1 | 0.1 | 0.1 |
| Total Concentration of Fine-Powdered Silicas (% by weight) | | 2.7 | 2.7 | 2.7 | 2.7 | 2.7 | 2.7 | 2.7 |
| Hydrophilic Fine-Powdered Silica/Hydrophobic Fine-Powdered Silica | | 0.7 | 0.7 | 0.4 | 0.4 | 0.4 | 0.7 | 0.7 |

The preparation method of blood testing containers containing separating compositions and the evaluation method were implemented in accordance with Example 1.

In respect of the cloudiness of partition wall, the presence or absence of cloudiness of the partition wall was visually inspected after the blood collection tube into which the blood was collected was refrigerated at 4° C. for one month.

(Evaluation Results)

The evaluation results of Examples 13 to 19 were put together in Tables 18 to 20.

TABLE 18

Evaluation Results of Serum or Plasma Separating Compositions about Specific Gravity

| | Examples | | | | | | |
|---|---|---|---|---|---|---|---|
| | 13 | 14 | 15 | 16 | 17 | 18 | 19 |
| Specific Gravity | 1.05 | 1.05 | 1.05 | 1.05 | 1.05 | 1.05 | 1.05 |

All of Examples 13 to 19 exhibited sufficient thixotropy and fluidity resistance.

On the other hand, in the blood evaluation using fresh human bloods, all of Examples 13 to 19 exhibited no crevice-like appearance in their partition walls after being centrifuged, and were satisfactory in respect of the mobility to partition wall-forming position, the presence/absence of hemolysis, the presence/absence of oily suspended matter or oily film, and the presence/absence of cloudiness during refrigeration of the blood samples.

It has been found from the above that the serum or plasma separating compositions of Examples 13 to 19, regardless of differences in liquid resin component, maintain sufficient thixotropy and fluidity resistance and simultaneously exhibit no crevice-like appearance in the partition wall after being centrifuged, are satisfactory in respect of the mobility to partition wall-forming position, the presence/absence of hemolysis and the presence/absence of oily suspended matter or oily film, and present no cloudiness in the partition walls even after the blood collection tubes after blood collection is preserved at 4° C. for one month.

TABLE 19

Evaluation Results of Blood Collection Tubes Containing Serum or Plasma Separating Compositions of Examples When Preserved Sideways at about 25° C. for One Week

| | | Examples | | | | | | |
|---|---|---|---|---|---|---|---|---|
| | | 13 | 14 | 15 | 16 | 17 | 18 | 19 |
| Viscous Properties at 25° C. | Viscosity (Pa · s) | 160 | 173 | 165 | 160 | 162 | 140 | 145 |
| | Value of Yield Stress (Pa) | 27 | 31 | 23 | 24 | 23 | 22 | 21 |
| Fluidity Resistance | Moving Distance (mm) | 0 | 1 | 0 | 1 | 1 | 1 | 1 |
| | Phase Separation | Absent | Absent | Absent | Absent | Absent | Absent | Absent |
| Separating Conditions | Mobility to Partition Wall-Forming Position | 3 | 3 | 3 | 3 | 3 | 3 | 3 |
| | Degree of Crevice-Like Appearance | 1 | 1 | 1 | 1 | 1 | 1 | 1 |
| | Cloudiness of Partition Wall | Absent | Absent | Absent | Absent | Absent | Absent | Absent |
| Hemolysis | | Absent | Absent | Absent | Absent | Absent | Absent | Absent |
| Oily Suspended Matter or Oily Film | | Absent | Absent | Absent | Absent | Absent | Absent | Absent |

TABLE 20

Evaluation Results of Blood Collection Tubes Containing Serum or Plasma Separating Compositions of Examples When Preserved Sideways at about 25° C. for Six Months

| | | Examples | | | | | | |
|---|---|---|---|---|---|---|---|---|
| | | 13 | 14 | 15 | 16 | 17 | 18 | 19 |
| Viscous Properties at 25° C. | Viscosity (Pa · s) | 163 | 175 | 167 | 162 | 165 | 141 | 146 |
| | Value of Yield Stress (Pa) | 28 | 31 | 24 | 24 | 23 | 22 | 22 |
| Fluidity Resistance | Moving Distance (mm) | 1 | 0 | 1 | 1 | 0 | 0 | 1 |
| | Phase Separation | Absent | Absent | Absent | Absent | Absent | Absent | Absent |
| Separating Conditions | Mobility to Partition Wall-Forming Position | 3 | 3 | 3 | 3 | 3 | 3 | 3 |
| | Degree of Crevice-Like Appearance | 1 | 1 | 1 | 1 | 1 | 1 | 1 |
| | Cloudiness of Partition Wall | Absent | Absent | Absent | Absent | Absent | Absent | Absent |
| Hemolysis | | Absent | Absent | Absent | Absent | Absent | Absent | Absent |
| Oily Suspended Matter or Oily Film | | Absent | Absent | Absent | Absent | Absent | Absent | Absent |

In Examples 13 to 19, to prevent the increase in yield value due to silica aggregation with time, the total content of hydrophilic and hydrophobic silicas was reduced to 2.7% by weight and the hydrophilic inorganic powder to hydrophobic inorganic powder ratio was set at 0.4 or 0.7. Furthermore, polyalkylene glycol of number average molecular weight of 10500 was added at a rate of 0.8% by weight in the above separating compositions. In Examples 14 to 19, purified water was also added at a rate of 0.1% by weight.

The invention claimed is:

1. A serum or plasma separating composition containing:
   a liquid resin component having a partition wall-forming capability;
   a hydrophilic inorganic powder;
   a hydrophobic inorganic powder; and
   an organic compound serving as a thixotropy enhancer, wherein
   the organic compound is a polyalkylene glycol and/or a derivative thereof and is made of at least one type of polymer selected from the group consisting of:
1) a homopolymer of a single type of monomer selected from $C_3$ to $C_5$ alkylene oxide monomers;
2) a random copolymer, an altering copolymer, or a periodic copolymer of two or more types of monomers selected from $C_2$ to $C_5$ alkylene oxide monomers;
3) a block copolymer of two or more types of monomers selected from $C_3$ to $C_5$ alkylene oxide monomers; and
4) a graft copolymer of at least one type of polymer of the polymers 1) to 3), the polyalkylene glycol and/or the derivative thereof has a number average molecular weight of 500 to 100000, both inclusive, and the content of the polyalkylene glycol and/or the derivative thereof in the total amount of the serum or plasma separating composition is 0.2% to 5% by weight, both inclusive.

2. The serum or plasma separating composition according to claim 1, further containing water.

3. The serum or plasma separating composition according to claim 1, wherein the ratio of the percent by weight of hydrophilic inorganic powder to the percent by weight of the hydrophobic inorganic powder is 0.2 to 1.0, both inclusive.

4. The serum or plasma separating composition according to claim 1, wherein the hydrophilic inorganic powder is hydrophilic silica and the hydrophobic inorganic powder is hydrophobic silica.

5. A blood testing container comprising: a container body; and the serum or plasma separating composition according to claim 1 contained in the container body.

6. The serum or plasma separating composition according to claim 2, wherein the ratio of the percent by weight of hydrophilic inorganic powder to the percent by weight of the hydrophobic inorganic powder is 0.2 to 1.0, both inclusive.

7. The serum or plasma separating composition according to claim 2, wherein the hydrophilic inorganic powder is hydrophilic silica and the hydrophobic inorganic powder is hydrophobic silica.

8. The serum or plasma separating composition according to claim 3, wherein the hydrophilic inorganic powder is hydrophilic silica and the hydrophobic inorganic powder is hydrophobic silica.

9. The serum or plasma separating composition according to claim 6, wherein the hydrophilic inorganic powder is hydrophilic silica and the hydrophobic inorganic powder is hydrophobic silica.

10. A blood testing container comprising: a container body; and the serum or plasma separating composition according to claim 2 contained in the container body.

11. A blood testing container comprising: a container body; and the serum or plasma separating composition according to claim 3 contained in the container body.

12. A blood testing container comprising: a container body; and the serum or plasma separating composition according to claim 4 contained in the container body.

13. A blood testing container comprising: a container body; and the serum or plasma separating composition according to claim 6 contained in the container body.

14. A blood testing container comprising: a container body; and the serum or plasma separating composition according to claim 7 contained in the container body.

15. A blood testing container comprising: a container body; and the serum or plasma separating composition according to claim 8 contained in the container body.

16. A blood testing container comprising: a container body: and the serum or plasma separating composition according to claim 9 contained in the container body.

* * * * *